United States Patent [19]
Steffee

[11] Patent Number: 5,443,514
[45] Date of Patent: Aug. 22, 1995

[54] METHOD FOR USING SPINAL INPLANTS

[75] Inventor: Arthur D. Steffee, Novelty, Ohio

[73] Assignee: AcroMed Corporation, Cleveland, Ohio

[21] Appl. No.: 130,288

[22] Filed: Oct. 1, 1993

[51] Int. Cl.6 .............................................. A61F 2/44
[52] U.S. Cl. .................................. 623/17; 128/898
[58] Field of Search .................... 623/16–21, 623/66; 606/60–64; 128/898

[56] References Cited

U.S. PATENT DOCUMENTS

| | | | |
|---|---|---|---|
| 4,834,757 | 5/1989 | Brantigan | 623/17 |
| 5,015,247 | 5/1991 | Michelson | 623/17 |
| 5,306,309 | 4/1994 | Wagner et al. | 623/17 |

FOREIGN PATENT DOCUMENTS

| | | | |
|---|---|---|---|
| 0560141 | 9/1993 | European Pat. Off. | 623/17 |
| 1107854 | 8/1984 | U.S.S.R. | 623/17 |

Primary Examiner—Randall L. Green
Assistant Examiner—Rob Clarke
Attorney, Agent, or Firm—Tarolli, Sundheim & Covell

[57] ABSTRACT

A method of fusing together the adjacent vertebrae using the spinal implant includes removing at least a portion of the spinal disc between the adjacent vertebrae. The spinal implant is inserted between the adjacent vertebrae with the first and second parallel side surfaces facing the adjacent vertebrae. The spinal implant is rotated into a position in which the parallel side surfaces extend from one of the adjacent vertebrae to the other adjacent vertebrae and the upper and lower surfaces engage the adjacent vertebrae.

7 Claims, 3 Drawing Sheets

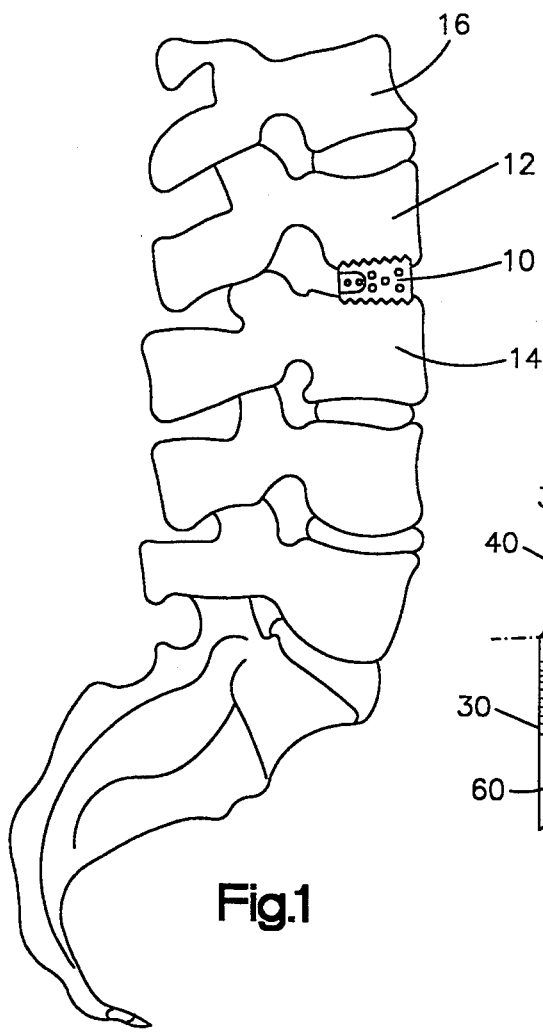
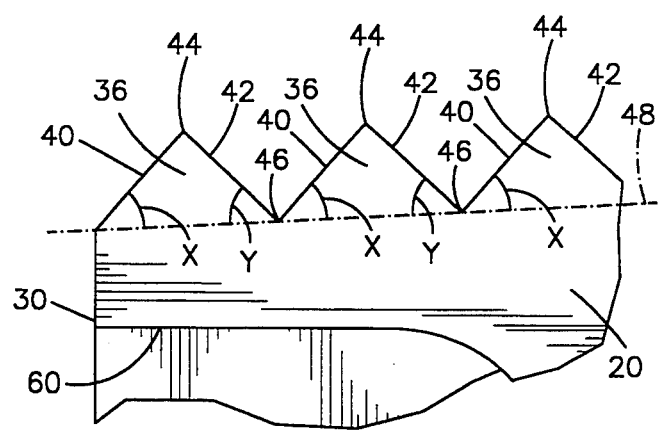
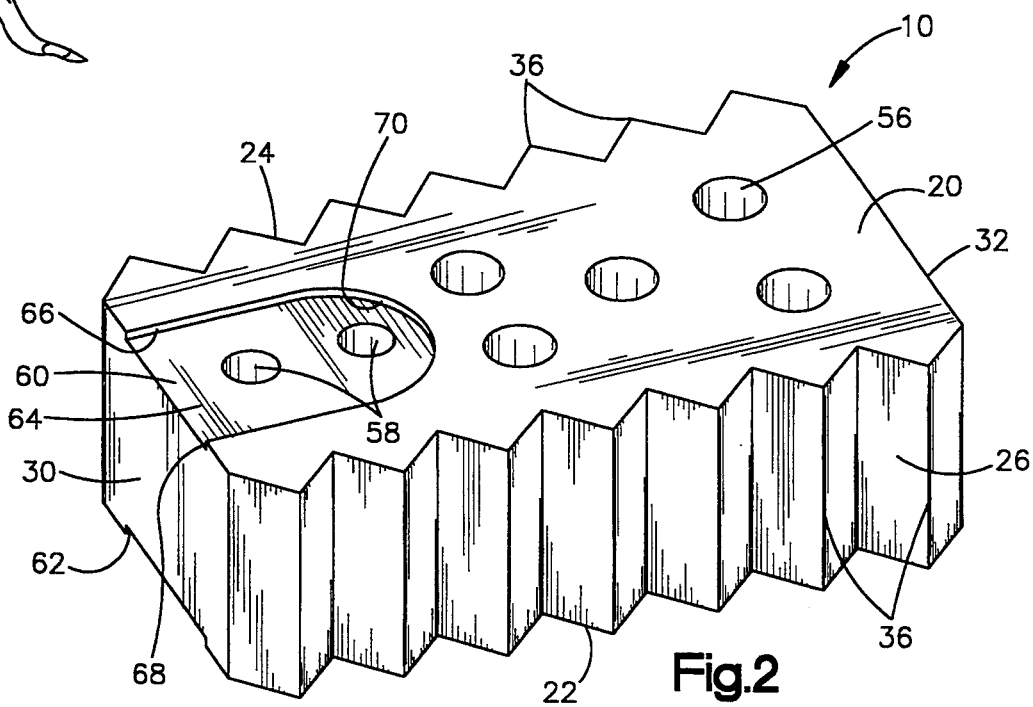

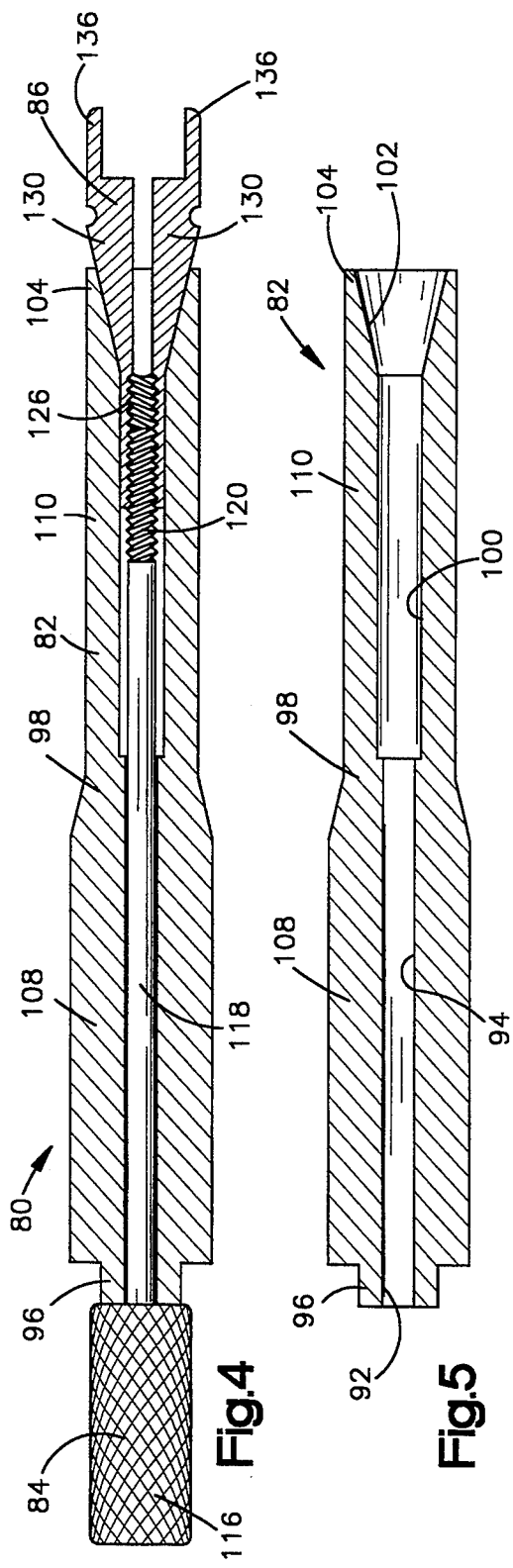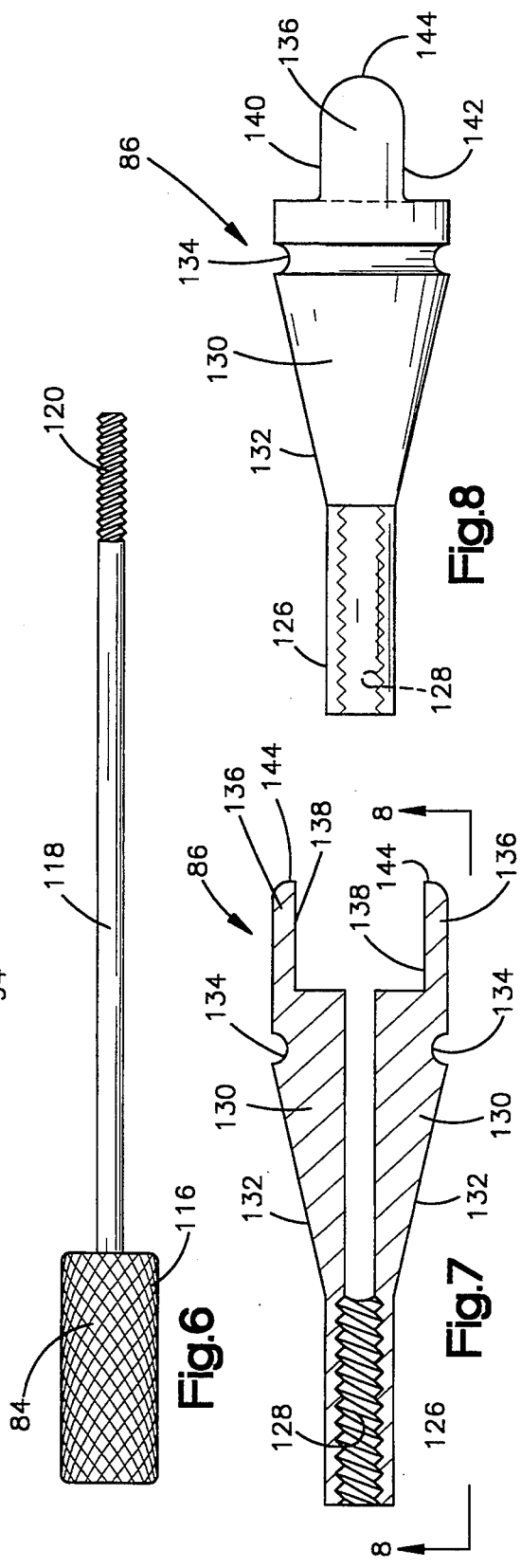

METHOD FOR USING SPINAL INPLANTS

BACKGROUND OF THE INVENTION

The present invention relates to a spinal implant, and to a method of using the spinal implant to fuse together adjacent vertebrae of a spinal column.

A known spinal implant has a rectangular shape and a tapered front end. The spinal implant includes nubs to grip adjacent vertebrae. The nubs have inclined front faces that accommodate forward sliding movement of the spinal implant into channels cut in the adjacent vertebrae. This known spinal implant is described in U.S. Pat. No. 4,834,757. By cutting channels into the vertebrae for receiving the spinal implant nerve roots are put at risk.

SUMMARY OF THE INVENTION

The present invention provides a new and improved spinal implant and method of using the spinal implant to fuse together adjacent vertebrae of a spinal column. The spinal implant of the present invention includes first and second side surfaces extending substantially parallel to each other. Upper and lower surface means for engaging the adjacent vertebrae extend between the first and second side surfaces and extend from a first end portion to a second end portion of the spinal implant. Recesses in the first and second side surfaces receive an instrument for rotating the spinal implant when the implant is located between the adjacent vertebrae.

The method of using the spinal implant to fuse together the adjacent vertebrae of a spinal column includes removing at least a portion of the spinal disc between the adjacent vertebrae. The spinal implant is inserted between the adjacent vertebrae with the first and second substantially parallel side surfaces facing the adjacent vertebrae. The spinal implant is rotated into a position in which the parallel side surfaces extend from one of the adjacent vertebrae to the other of the adjacent vertebrae and the upper and lower surface means engage the adjacent vertebrae. There are no channels cut in the adjacent vertebrae. Thus, the operation takes less time and lessens the risks to the patient.

BRIEF DESCRIPTION OF THE DRAWINGS

The foregoing and other features of the present invention will become more apparent to one skilled in the art upon reading the following description of the present invention with reference to the accompanying drawings, wherein:

FIG. 1 is an elevation view of a human spinal column having a spinal implant in accordance with that of the present invention placed therein;

FIG. 2 is a perspective view of the spinal implant of FIG. 1;

FIG. 3 is an enlarged plan view looking at a portion of the spinal implant of FIG. 2 from the side;

FIG. 4 is a sectional view of an instrument for holding the spinal implant of FIG. 2 to facilitate inserting the spinal implant between adjacent vertebrae and rotating the spinal implant;

FIG. 5 is a sectional view of an intermediate portion of the instrument of FIG. 4;

FIG. 6 is a plan view of a handle of the instrument of FIG. 4;

FIG. 7 is a sectional view of a clamp portion of the instrument of FIG. 4;

FIG. 8 is a plan view of the clamp portion of FIG. 7 taken along the line 8—8 of FIG. 7;

DESCRIPTION OF A PREFERRED EMBODIMENT

Figure 9:
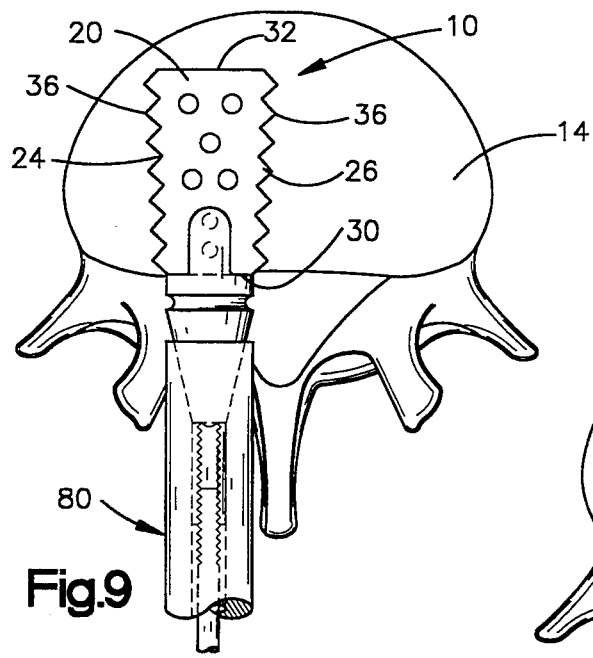
FIG. 9 is a view showing a method of inserting spinal implants in a side-by-side relationship between adjacent vertebrae.

One or a pair of substantially rigid spinal implants 10 (one of which is shown in FIG. 1) are placed between adjacent vertebrae 12 and 14 of a spinal column 16 in a side-by-side relationship to fuse together the adjacent vertebrae. Preferably, the spinal implants 10 are made by injection molding a chopped carbon fiber reinforced polymer. However, the spinal implants 10 can be made of other suitable implantable materials such as stainless steel or titanium. Also, preferably, the ultimate tensile strength of the material used to make the spinal implants 10 is higher than 10,000 psi so that the spinal implants will prevent relative movement between the adjacent vertebrae 12 and 14 and will support the compressive load of the spinal column.

Each of the spinal implants 10 (FIG. 2) has parallel side surfaces 20 and 22. An upper surface 24 and a lower surface 26 for engaging the adjacent vertebrae 12 and 14 extend between the side surfaces 20 and 22. The upper and lower surfaces 24 and 26 adjacent a first end portion 30 of the spinal implant 10 are spaced apart by a first distance. The upper and lower surfaces 24 and 26 adjacent a second end portion 32 of the spinal implant 10 are spaced apart a second distance. The second distance is preferably greater than the first distance to give the spinal implant a wedge shape for use in portions of the spine with a lordotic curve.

The upper and lower surfaces 24 and 26 include a plurality of triangular-shaped teeth 36 that extend from the side surface 20 to the side surface 22 for engaging the vertebrae 12 and 14. Each tooth 36 (FIG. 3) includes a surface 40 facing toward the end portion 30. A surface 42 of the tooth 36 faces the end portion 32 of the spinal implant 10. The surfaces 40 and 42 of the tooth 36 intersect each other to form an edge 44. The surfaces 40 and 42 of adjacent teeth 36 intersect to form edges 46. The edges 46 are parallel to each other and lie in a plane 48.

The surface 40 of the tooth 36 extends at an acute angle x to the plane 48. The surface 42 of the tooth 36 extends at an acute angle y to the plane 48. Preferably, the angles x and y are equal and have a value of 45° so that surfaces 40 and 42 extend perpendicular to each other. Therefore, the teeth 36 are not preferential. The teeth 36 prevent the spinal implant 10 from moving toward the anterior portion of the spinal column 16 as much as they prevent the spinal implant from moving toward the posterior portion of the spinal column 16.

A plurality of openings 56 and 58 extend from the side surface 20 to the side surface 22 to provide for blood flow and bone growth from one side of the implant 10 to the other side of the implant. The openings 58 are located near the end portion 30 of the implant.

The openings 56 and 58 extend perpendicular to the side surfaces 20 and 22. Preferably, there are five openings 56 and two openings 58 extending between the sides 20 and 22. The openings 56 have diameters larger than the diameters of the openings 58. The sizes of the diameters of the openings 56 and 58 may be any size that allows tissue ingrowth and blood flow between the side surfaces 20 and 22 of the implant 10.

The side surface 20 includes a recess 60 and the side surface 22 includes a recess 62. The openings 58 are located in the recesses 60 and 62. Each of the recesses 60 and 62 includes a planar bottom surface 64. The recesses 60 and 62 also include parallel side surfaces 66 and 68 extending perpendicular to the bottom surface 64 and from the end portion 30 of the spinal implant 10 toward the end portion 32. An arcuate side surface 70 extends between the parallel side surfaces 66 and 68. The recesses 60 and 62 in the side surfaces 20 and 22 are for receiving an instrument 80 (FIG. 4) that holds the spinal implant 10 to facilitate insertion of the spinal implant in between the adjacent vertebrae 12 and 14 and rotation of the spinal implant once between the adjacent vertebrae.

Any instrument that firmly holds the implant and permits the implant to be rotated into position can be used. One such instrument 80 (FIG. 4) includes an intermediate portion 82 (FIG. 5), a handle 84 (FIG. 6) and a clamp portion 86 (FIGS. 7 and 8).

The intermediate portion 82 (FIG. 5) is generally cylindrical and includes an opening 92 extending along the axis of the intermediate portion. The opening 92 includes a first cylindrical portion 94 extending from an end portion 96 of the intermediate portion 82 to a central portion 98. A second cylindrical portion 100 of the opening 92 extends from the first cylindrical portion 94 to a tapered portion 102 of the opening 92. The second cylindrical portion 100 of the opening 92 has a diameter larger than the diameter of the first cylindrical portion 94. The tapered portion 102 of the opening 92 tapers from a small diameter adjacent the portion 100 to a larger diameter adjacent an end portion 104 of the intermediate portion 82.

The intermediate portion 82 includes a large outer diameter portion 108 that extends from the end portion 96 to the central portion 98. The portion 108 tapers from a large outer diameter to a small outer diameter portion 110 which extends from the portion 108 to the end portion 104. The outer surface of the portion 108 is preferably knurled to provide for easy gripping of the intermediate portion 82 by a surgeon. The end portion 96 has a diameter which is smaller than the portions 108 and 110.

The handle 84 (FIG. 6) has a large diameter knurled portion 116. A small diameter shaft 118 extends from the knurled portion 116. The shaft 118 has a threaded end 120 for threadably engaging the clamp portion 86.

The clamp portion 86 (FIGS. 7 and 8) includes a stem 126 with an internally threaded opening 128 for receiving the threaded end 120 of the handle 84. A pair of clamp halves 130 are spaced apart and extend from the stem 126. The clamp halves 130 have outwardly tapering surfaces 132. The surfaces 132 taper from the stem 126 to a groove 134.

The clamp halves 130 include extensions 136 which are received in the recesses 60 and 62 in the side surfaces 20 and 22 of the spinal implant 10. The extensions 136 include planar inner surfaces 138 (FIG. 7) for engaging the bottom planar surfaces 64 of the recesses 60 and 62.

Parallel side surfaces 140 and 142 (FIG. 8) of the extensions 136 engage side surfaces 66 and 68 of the recesses 60 and 62 when the instrument 80 is used to hold the spinal implant 10. Arcuate side surface 144 for engaging the side surface 70 extends between the side surfaces 140 and 142.

The shaft 118 of the handle 84 extends into the opening 92 in the intermediate portion 82 and threadably engages the stem 126 of the clamp portion 86 (FIG. 4). As the handle 84 is threaded into the opening 128 of the clamp portion 86, the clamp portion is drawn into the opening 92 in the intermediate portion 82. The tapered surfaces 132 of the clamp halves 130 engage the tapered portion 102 of the opening 92. As the clamp portion 86 is drawn into the opening 92, the clamp halves 130 are forced toward each other by the tapered portion 102 of the opening 92 to clamp the spinal implant 10 between the extensions 136.

The method of placing the spinal implants 10 between the adjacent vertebrae 12 and 14 to fuse together the adjacent vertebrae will now be described. Most of the spinal disc located between the vertebrae 12 and 14 is removed. The facing surfaces of the vertebrae 12 and 14 are cleaned with a disc shaver and rongeurs. Preferably, an annulus of the spinal disc is left between the vertebrae 12 and 14.

Figure 10:
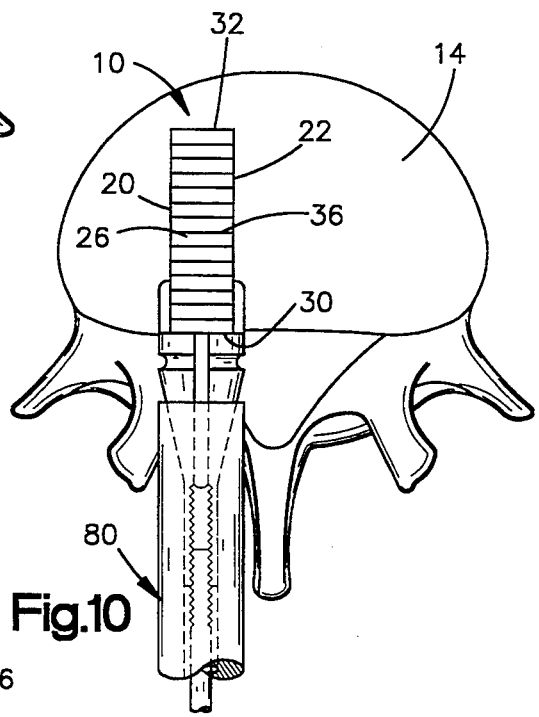
FIG. 10 is a view similar to FIG. 9 further showing the method of inserting the spinal implants between the adjacent vertebrae.

The instrument 80 is used to hold a spinal implant 10. The spinal implant 10 is inserted posteriorly or anteriorly between the vertebrae 12 and 14 with the parallel sides surfaces 20 and 22 facing the adjacent vertebrae 12 and 14 (FIG. 9). The spinal implant 10 is inserted so that the end portion 32 is near the anterior side of the spinal column 16 and the end portion 30 is near the posterior side of the spinal column. The spinal implant 10 is rotated 90° to the position shown in FIG. 10 so that the teeth 36 on the upper and lower surfaces 24 and 26 engage the vertebrae 12 and 14 and the side surfaces 20 and 22 extend from the vertebra 12 to the vertebra 14. The wedge shape of the spinal implant 10 alleviates the need to distract the posterior portion of the spine segment a large distance and then compress the posterior portion to achieve the required lordosis. The posterior portion only needs to be distracted to the desired interdiscal height.

Figure 11:
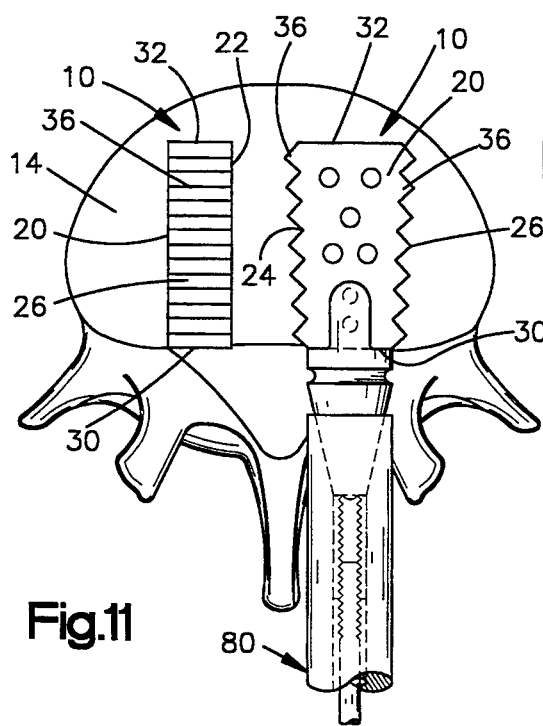
FIG. 11 is a view similar to FIG. 10 further showing the method of inserting the spinal implants between the adjacent vertebrae.
Figure 12:
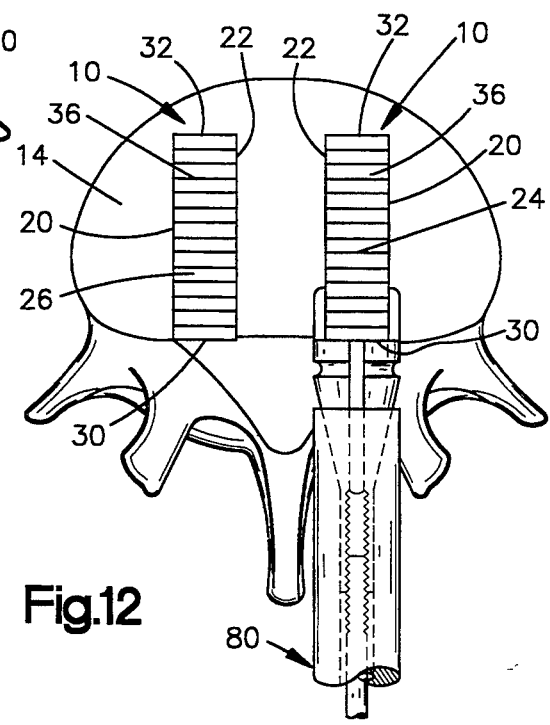
FIG. 12 is a view similar to FIG. 11 further showing the method of inserting the spinal implants between adjacent vertebrae.

A second spinal implant 10 is inserted between the vertebra 12 and 14 in a side-by-side relationship with the spinal implant. The second spinal implant 10 is inserted in a similar manner as the first implant. The instrument 80 is used to hold the spinal implant 10. The spinal implant 10 is inserted with the parallel side surfaces 20 and 22 facing the vertebrae 12 and 14 (FIG. 11). The second spinal implant 10 is then rotated 90° to the position shown in FIG. 12 so that the teeth 36 of the upper and lower surfaces 24 and 26 engage the vertebrae 12 and 14.

The remaining space between the spinal implants 10 and the adjacent vertebrae 12 and 14 is packed with autograft or allograft bone. An apparatus for maintaining the vertebrae 12 and 14 in a desired spatial relationship such as that disclosed in U.S. Pat. No. 4,696,290 is attached to the spinal column 16 until the vertebrae 12 and 14 have completely fused together. The apparatus for maintaining the vertebrae 12 and 14 in the desired spatial relationship prevents the spinal implants 10 from moving out of position and the bone graft from falling out of the spaces between the spinal implants and the vertebrae 12 and 14.

From the above description of the invention, those skilled in the art will perceive improvements, changes and modifications. Such improvements, changes and modifications within the skill of the art are intended to be covered by the appended claims.

Having described the invention, the following is claimed:

1. A method of fusing together adjacent vertebrae of a spinal column comprising the steps of:

removing at least a portion of the disc between the adjacent vertebrae;

providing a spinal implant with first and second side surfaces substantially parallel to each other and upper and lower surface means extending between the first and second side surfaces;

inserting the spinal implant between the adjacent vertebrae with the first and second substantially parallel side surfaces of the spinal implant facing the adjacent vertebrae; and rotating the spinal implant into a position in which the parallel side surfaces of the spinal implant extend from one of the adjacent vertebrae to the other adjacent vertebrae and the upper and lower surface means engage the adjacent vertebrae.

2. A method as set forth in claim 1 further including providing the spinal implant with first and second end portions wherein the upper and lower surface means are spaced apart by a first distance adjacent the first end portion and are spaced apart by a second distance greater than the first distance adjacent the second end portion.

3. A method as set forth in claim 2 wherein said step of inserting the spinal implant includes inserting the spinal implant from the posterior side of the spinal column into a position in which the first end portion of the spinal implant is located adjacent the posterior side of the spinal column and the second end portion of the spinal implant is located adjacent the anterior side of the spinal column.

4. A method as set forth in claim 1 wherein said step of inserting the spinal implant includes inserting two spinal implants in a side-by-side relationship.

5. A method as set forth in claim 1 further including the step of packing bone graft around the spinal implant after said step of rotating the spinal implant.

6. A method as set forth in claim 1 further including the step of attaching an apparatus to the spinal column for maintaining a desired spatial relationship of the adjacent vertebrae.

7. A method as set forth in claim 1 wherein said step of removing at least a portion of the spinal disc includes leaving an annulus of the disc around the peripheries of the adjacent vertebrae.

* * * * *